(12) United States Patent
Tanaka (10) Patent No.: US 6,629,051 B2
(45) Date of Patent: Sep. 30, 2003

(54) DEFECT INSPECTION DATA PROCESSING SYSTEM

(75) Inventor: Toshihiko Tanaka, Komagane (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/910,747

(22) Filed: Jul. 23, 2001

(65) Prior Publication Data

US 2002/0024659 A1 Feb. 28, 2002

Related U.S. Application Data (63) Continuation of application No. PCT/JP00/08251, filed on Nov. 22, 2000.

(30) Foreign Application Priority Data

Nov. 25, 1999 (JP) ............................................. 11-334849

(51) Int. Cl.[7] ................................................. G06F 11/32
(52) U.S. Cl. ...................... 702/81; 250/201.9; 356/237; 382/145; 382/149
(58) Field of Search ...................... 702/81–84, 183–185; 700/108–111; 356/237, 237.2; 382/141, 145, 149; 250/201.3

(56) References Cited

U.S. PATENT DOCUMENTS

| | | | |
|---|---|---|---|
| 5,694,214 A | * 12/1997 | Watanabe et al. | ............ 356/237 |
| 5,943,437 A | * 8/1999 | Sumie et al. | ................ 382/149 |
| 5,963,314 A | * 10/1999 | Worster et al. | ........... 356/237.2 |
| 6,248,988 B1 | * 6/2001 | Krantz | ..................... 250/201.3 |
| 6,330,352 B1 | * 12/2001 | Ishikawa et al. | ............. 382/141 |
| 6,400,839 B1 | * 6/2002 | Takayama | ................... 382/145 |
| 6,456,951 B1 | * 9/2002 | Maeda et al. | .................. 702/81 |

FOREIGN PATENT DOCUMENTS

| | | |
|---|---|---|
| JP | 4-285845 A | 10/1992 |
| JP | 5-45300 A | 2/1993 |
| JP | 6-341960 A | 12/1994 |
| JP | 8-147408 A | 6/1996 |
| JP | 8-278256 A | 10/1996 |
| JP | 8-321700 A | 12/1996 |
| JP | 9-61365 A | 3/1997 |
| JP | 9-145633 A | 6/1997 |
| JP | 11-194996 A | 7/1999 |
| JP | 11-195105 A | 7/1999 |

OTHER PUBLICATIONS

Tanaka, "Defect inspection system", Appl. No.: 09/917,845, Pub. No.: US 2002/0009220 A1, Pub. Date: Jan. 24, 2002.*
Official Action dated Feb. 14, 2002 issued in counterpart Singapore application No. SG 200104486–6, filed Nov. 22, 2000.

* cited by examiner

Primary Examiner—John Barlow
Assistant Examiner—John Le
(74) Attorney, Agent, or Firm—Frishauf, Holtz, Goodman & Chick, P.C.

(57) ABSTRACT

A defect inspection data processing system includes a client computer having an image pickup section for picking up a two-dimensional image of a to-be-inspected object to be processed in a manufacturing process, and a data transfer section for transferring data indicative of the image picked by the image pickup section. A database stores image data transferred from the client computer. The system also includes a host computer having a defect extraction section for extracting defect information from the image data stored in the database, and a good/bad judgment section for judging whether or not the to-be-inspected object is good, on the basis of the defect information extracted by the defect extraction section. The client computer is separate from the host computer and connected thereto via a communication line.

14 Claims, 3 Drawing Sheets

DEFECT INSPECTION DATA PROCESSING SYSTEM

CROSS REFERENCE TO RELATED APPLICATIONS

This is a Continuation Application of PCT application Ser. No. PCT/JP00/08251, filed Nov. 22, 2000, which was not published under PCT Article 21(2) in English.

This application is based upon and claims the benefit of priority from the prior Japanese Patent Application No. 11-334849, filed Nov. 25, 1999, the entire contents of which are incorporated herein by reference.

BACKGROUND OF THE INVENTION

1. Field of the Invention

The present invention relates to a defect inspection data processing system for processing data obtained from defect inspection on a surface of a semiconductor wafer or a liquid crystal glass substrate, etc.

2. Description of the Related Art

In general, while a semiconductor wafer or a liquid crystal glass substrate is being manufactured, a patterned resist is provided on a silicon or glass substrate with a film interposed therebetween.

If, in such a photolithography process, the resist on the substrate is uneven in thickness or dust is adhered thereto, defects, such as unevenness in the line width of a pattern after etching, or occurrence of pinholes, may occur.

To avoid this, in a substrate manufacturing process before etching, all substrates are usually subjected to an inspection for detecting a defect. As a method for inspecting all substrates, a method of workers visually checking the substrates is often employed. However, when using workers to visually inspect the substrates, the dissimilarity in the checking ability of each worker, as well as the influence of dust from the bodies of workers in a clean room cannot be ignored. In light of this, a method for observing substrates at as far a distance as possible, or a method for imparting a defect inspecting function to an apparatus is proposed.

Figure 4:
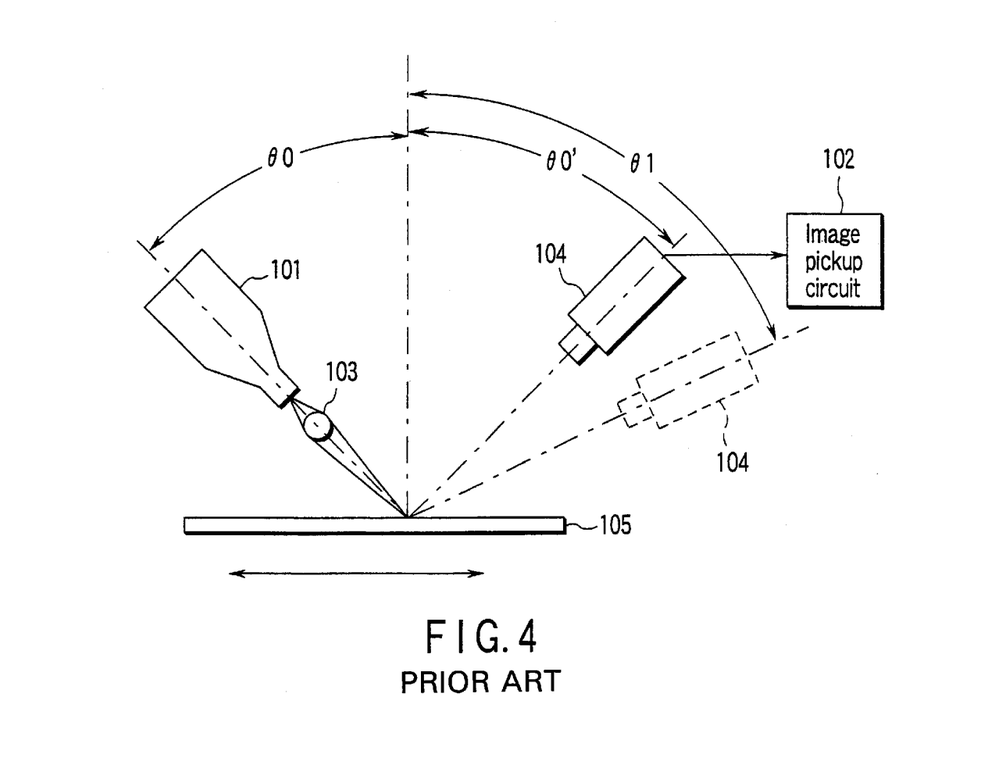
FIG. 4 is a view illustrating an example of a nal defect inspection apparatus.

FIG. 4 is a view illustrating an example of a defect inspection apparatus for detecting a defect on a surface of a to-be-inspected object, disclosed in Japanese Patent Application KOKAI Publication No. 09-061365. An illumination section 101 has an illumination light source and an optical system. As the illumination light source, a lamp housing is used which contains a halogen lamp, a heat-wave absorbing filter and a condenser lens. Further, the optical illumination system comprises a condenser lens for converging a light flux from the lamp housing and a fiber bundle.

The illumination section 101 emits illumination light to a to-be-inspected object 105 at incident angle θ0. A cylindrical lens 103 for converging a light flux is interposed between the illumination section 101 and the to-be-inspected object 105. A line sensor camera 104 is provided in a position opposed to the illumination section 101. The line sensor camera 104 picks up an image of a linear area of the illuminated object 105.

The to-be-inspected object 105 is moved in a direction indicated by the arrow in the figure, and an image picked up by the line sensor camera 104 in synchronism with the movement is supplied to an image pickup circuit 102. The image pickup circuit 102 forms a two-dimensional image and supplies it to a host computer (not shown). The line sensor camera 104 has a structure that enables the angle between the camera and the surface of the to-be-inspected object 105 to be changed. For example, if the angle is set equal to the reflection angle θ1 of the illumination section 101, the surface of the to-be-inspected object 105 can be picked up.

After that, images of the to-be-inspected object 105, picked up in synchronism with the movement of the object, with the reflection angle of the illumination section 101 set at θ0' (=θ0) and θ1, are subjected to image processing by the host computer. As a result, a defect such as the unevenness of a film on the to-be-inspected object 105 or dust attached thereto is extracted and compared with an acceptability criterion that is one of the inspection conditions, thereby determining whether or not the to-be-inspected object 105 is defective.

In the above-described defect inspection apparatus, a defect image pickup section including the illumination section 101 and the line sensor camera 104 is connected to the host computer for determining, for example, whether or not the to-be-inspected object is defective. The defect inspection apparatus including the defect image pickup section and host computer are installed in a clean room. In the clean room, air is downwardly flown from an upper portion of the room through an air-cleaning filter, thereby preventing, for example, dust particles from adhering to the to-be-inspected object and hence the influence of the dust particles upon defect inspection.

However, in the above structure, one computer is provided for one defect image pickup section. Therefore, if a plurality of defect inspection apparatuses are prepared to increase the inspection efficiency, it is necessary to accommodate the same number of defect image pickup sections and host computers in the clean room. This means that the clean room must be large. Accordingly, the entire equipment involves an increase in costs, which is economically disadvantageous. Furthermore, since other apparatuses including the host computer are located in the clean room, together with the defect image pickup section, workers come into and out of the clean room, which limits the dust preventing effect.

Where a defect inspection apparatus is provided for each process executed in the clean room, different inspectors operate host computers respectively connected to different defect inspection apparatuses. Since the inspectors usually have different criterions for defect determination, the accuracy of the entire defect inspection is reduced. Also, where clean rooms are located along the manufacture lines of respective factories remote from each other, it is very possible that different criterions will be used for defect inspection in different factories. As a result, the efficiency and accuracy of defect inspection are reduced.

It is the object of the invention to provide an economical and compact defect inspection data processing system that enables a plurality of defect inspection apparatuses to execute efficient and accurate defect inspection.

BRIEF SUMMARY OF THE INVENTION (1) A defect inspection data processing system according to the invention comprises: a client computer including image pickup means for picking up a two-dimensional image of a to-be-inspected object to be processed in a manufacturing process, and data transfer means for transferring data indicative of the image picked by the image pickup means; a database for storing image data transferred from the client computer; and a host computer including defect extraction means for extracting defect information from the image data read from the database, and good/bad judgment means for judging whether or not the to-be-inspected object is good, on the basis of the defect information extracted by the defect extraction means, the client computer being separate from the host computer and connected thereto via a communication line.

(2) The defect inspection data processing system of the present invention is a system according to item (1), in which the good/bad judgment means has a function of comparing the defect information extracted by the defect extraction means with defect data registered in a predetermined defect dictionary, thereby determining the type of defect, and a function of registering new defect data in the defect dictionary.

(3) The defect inspection data processing system of the present invention is a system according to item (1), in which the database is connected to the communication line, thereby storing, in the database, image data transmitted thereto from the client computer via the communication line, and transferring the image data, stored in the database, to the host computer via the communication line.

(4) The defect inspection data processing system of the present invention is a system according to item (1), in which the communication line is connected to a plurality of client computers.

(5) The defect inspection data processing system of the present invention is a system according to item (3), in which the communication line is connected to a plurality of client computers.

(6) The defect inspection data processing system of the present invention is a system according to item (1) or (3), in which the host computer is located in a place different from a place in which the client computer is located, the host and client computers being connected via the communication line.

(7) The defect inspection data processing system of the present invention is a system according to item (1) or (3), in which the client computer is located in a clean room for executing the manufacturing process, and the host computer is located outside the clean room and separate from the client computer.

(8) The defect inspection data processing system of the present invention is a system according to item (4), in which the plurality of client computers are located in different areas and connected to the host computer via the communication line.

(9) The defect inspection data processing system of the present invention is a system according to item (1), in which the client computer includes defect extraction means for extracting a defective portion from image data picked by the image pickup means.

(10) The defect inspection data processing system of the present invention is a system according to any one of items (3), (4) and (5), in which the client computer includes defect extraction means for extracting a defective portion from image data picked by the image pickup means.

(11) The defect inspection data processing system of the present invention is a system according to item (1), in which the host computer includes an image storage for storing image data picked by the image pickup means, and a defect detection algorism formed of a plurality of defect extraction means for processing, in a parallel manner, a plurality of different image data items stored in the image storage.

(12) The defect inspection data processing system of the present invention is a system according to any one of item (1), (9) and (11), in which the defect extraction means includes image nonuniformity removing means for removing image nonuniformity from the image data.

(13) The defect inspection data processing system of the present invention is a system according to item (10), in which the defect extraction means includes image nonuniformity removing means for removing image nonuniformity from the image data.

(14) The defect inspection data processing system of the present invention is a system according to item (12), in which the image nonuniformity removing means includes image nonuniformity storage means for acquiring, from the image pickup means, a sample image having a nondefective mirror surface or having a uniform reflectance over an entire surface thereof, and storing image nonuniformity data on the sample image, the image nonuniformity removing means removing the image nonuniformity data from image data read from the database.

(15) The defect inspection data processing system of the present invention is a system according to any one of item (1), (9) and (11), in which the defect extraction means further includes feature storage means for storing an image and coordinates of a characterizing portion of the to-be-inspected object, which determines coordinates of the to-be-inspected object, characterizing-portion-extracting means for comparing an image, stored in the feature storage means, with image data read from the database, thereby obtaining a displacement therebetween, and image position correcting means for correcting the image displacement detected by the characterizing-portion-extracting means.

(16) The defect inspection data processing system of the present invention is a system according to item (10), in which the defect extraction means further includes feature storage means for storing an image and coordinates of a characterizing portion of the to-be-inspected object, which determines coordinates of the to-be-inspected object, characterizing-portion-extracting means for comparing an image, stored in the feature storage means, with image data read from the database, thereby obtaining a displacement therebetween, and image position correcting means for correcting the image displacement detected by the characterizing-portion-extracting means.

(17) The defect inspection data processing system of the present invention is a system according to item (1), in which the communication line is connected to operation/input means for supplying an instruction to the client computer by remote control.

(18) The defect inspection data processing system of the present invention is a system according to item (1), in which the host computer automatically stores, in the database, image data determined defective by the good/bad judgment means.

(19) The defect inspection data processing system of the present invention is a system according to item (1), in which the image pickup means is formed of a line illumination unit and a line sensor camera, which can move relative to the to-be-inspected object to obtain an image of an entire surface of the to-be-inspected object, an angle of an optical axis of each of the line illumination unit and the line sensor camera relative to the surface of the to-be-inspected object being able to be changed to obtain different image data items.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently embodiments of the invention, and together with the general description given above and the detailed description of the embodiments given below, serve to explain the principles of the invention.

DETAILED DESCRIPTION OF THE INVENTION

The embodiment of the invention will be described with reference to the drawings.

Figure 1:
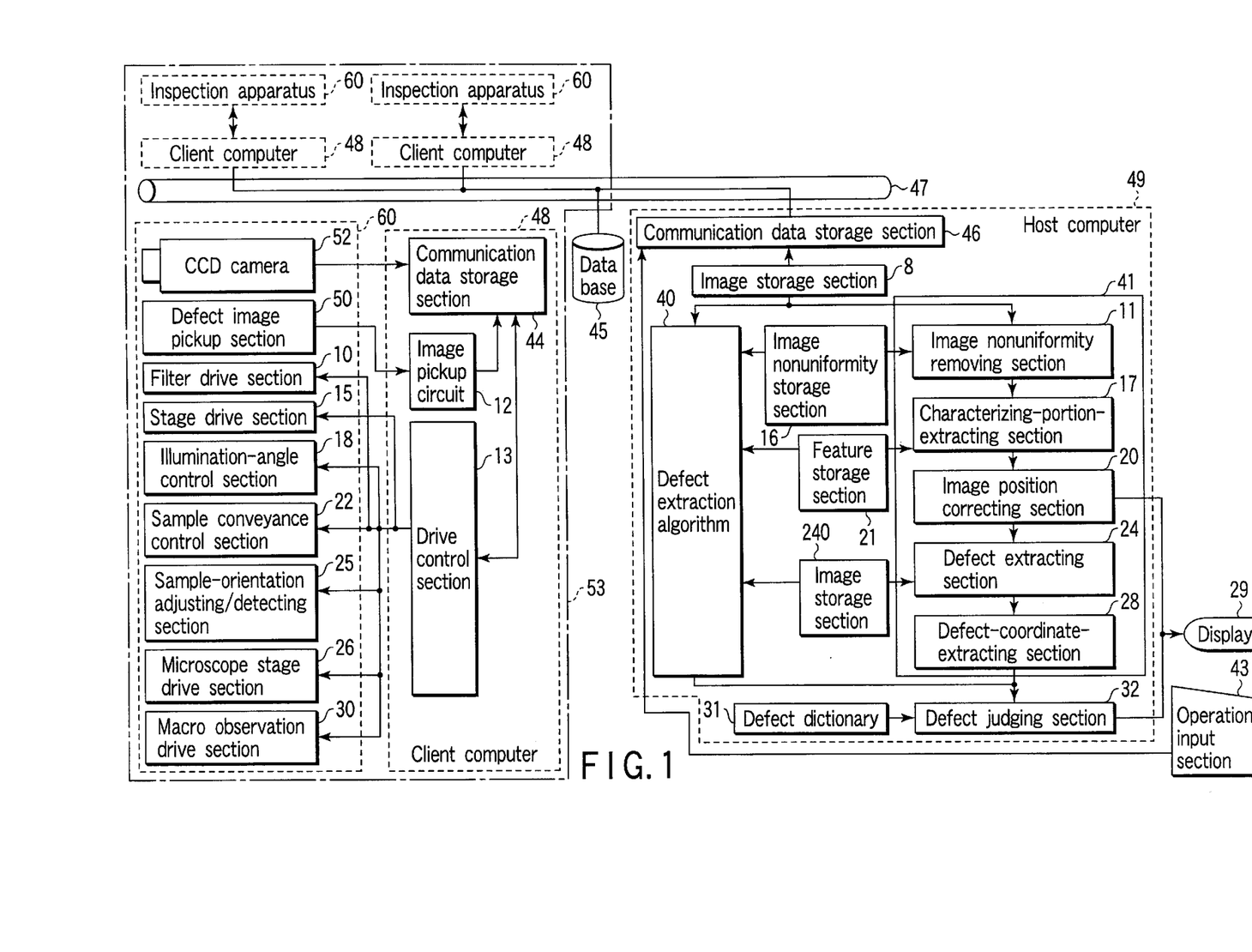
FIG. 1 is a schematic view illustrating a structure of a defect inspection data processing system according to the embodiment of the invention.

FIG. 1 is a schematic view illustrating a structure of a defect inspection data processing system according to the embodiment of the invention. In FIG. 1, a LAN (in-company network) 47 is connected to a plurality (three in the shown case) of client computers 48 that are connected to respective inspection apparatuses 60 used in respective manufacturing processes, and is also connected to a single host computer 49. The plurality of client computers 48 and the single host computer 49 can exchange images and/or data with each other by communication executed via the LAN 47. Further, the LAN 47 is also connected to a database 45 having a large capacity storage medium. The database 45 stores image data supplied from each client computer 48, and various types of data such as a recipe supplied from the host computer 49.

Each client computer 48 is located in a clean room 53 in which the manufacturing processes are performed, together of the main body of a corresponding inspection apparatus 60. Each client computer 48 includes an image pickup circuit 12, a drive control section 13 and a communication data storage 44. The image pickup circuit 12 and the drive control section 13 are connected to the communication data storage 44, which is connected to the LAN 47. The image pickup circuit 12 connects data items of one line picked by a line sensor camera 4 incorporated in a defect image pickup section 50 described later, thereby inputting an entire image of a to-be-inspected object 5 as a single two-dimensional image. The drive control section 13 executes control for moving the to-be-inspected object 5, described later, and controls various drive sections for driving the optical system. The communication data storage 44 exchanges images and various types of data via the LAN 47.

The image pickup circuit 12 is connected to the defect image pickup section 50. The drive control section 13 is connected to a filter drive section 10 for moving a filter 7 to cross the optical path or moving it away therefrom in the defect image pickup section 50, which will be described later. The drive control section 13 is also connected to a stage drive section 15 for driving a stage (not shown) for mounting thereon the to-be-inspected object 5, and connected to an illumination angle adjusting section 18 for adjusting the angle of the illumination section 1 with respect to the to-be-inspected object 5. The drive control section 13 is further connected to a sample conveyance control section 22, a sample-orientation adjusting/detecting section 25, a microscope stage drive section 26 and a macro-observation control section 30, etc. The communication data storage 44 is directly connected to a CCD camera 52.

On the other hand, the host computer 49 is located outside the clean room 53, together with, for example, the database 45. In other words, the host computer 49 and the database 45 are located in a place different and remote from the place of each client computer 48. The host computer 49 has a communication data storage 46. The communication data storage 46 is connected to the LAN 47. The communication data storage 46 is also connected to an image storage 8, which is connected to defect extraction algorithms 40 and 41.

The communication data storage 46 exchanges images and data via the LAN 47. The image storage 8 stores images stored in the database 45 and created by each client computer 48, and can read and write a voluntarily selected image. The defect extraction algorithms 40 and 41 have respective algorithms similar to each other, and can process, in a parallel manner, different image data items obtained by combining incident angles θ0 and θ1 of light emitted from the illumination section 1 with respect to the to-be-inspected object 5, and the use or nonuse of the filter 7 across the optical path, which will be described later.

The defect extraction algorithms 40 and 41 each have an image nonuniformity removing section 11, a characterizing-portion extracting section 17, an image position correcting section 20, a defect extracting section 24 and a defect coordinate extracting section 28. The defect extraction algorithms 40 and 41 receive image data from the image storage 8 and extract a defect therefrom.

The image nonuniformity removing section 11 corrects an image, read from the image storage 8, into a correct image of the to-be-inspected object resulting from reflection, using data concerning image nonuniformity stored in an image nonuniformity storage 16, described later.

The characterizing-portion extracting section 17 compares portions of an image stored in a feature storage 21, described later, with corresponding portions of an image corrected by the image nonuniformity removing section 11, thereby detecting whether or not the coordinates of a plurality of portions of a to-be-inspected object included in the corrected image are deviated vertically or in a direction of rotation.

The image position correcting section 20 executes image processing to move the image of the to-be-inspected object vertically or in the direction of rotation so as to correct the deviations detected by the characterizing-portion extracting section 17. As a result, the to-be-inspected object is always displayed to have the same coordinates.

The defect extracting section 24 removes, from the image processed by the image position correcting section 20, a to-be-inspected object outline image or a particular pattern image, etc., which is an image inherent in the to-be-inspected object, thereby extracting a defective portion.

The defect coordinate extracting section 28 detects features, such as coordinates, size and tine, etc., of the defective portion extracted by the defect extracting section 24. Information on these features is supplied to the drive control section 13 of each client computer 48 as described later.

The image nonuniformity storage 16 is connected between the respective image nonuniformity removing sections 11, 11 of the defect extraction algorithms 40 and 41 (the image nonuniformity removing section 11 of the algorithm 40 is not shown). The feature storage 21 is connected between the respective the characterizing-portion extracting sections 17, 17 (the section 17 of the algorithm 40 is not shown). An image storage 240 is connected between the respective defect extracting sections 24, 24 (the defect extracting section of the algorithm 40 is not shown).

The image nonuniformity storage 16 stores data created by the line sensor camera 4, when there is no to-be-inspected object 5 as described later, or when picking up a to-be-inspected object having an ideal mirror surface (a nondefective mirror surface), a master substrate with no defects, or a sample having a surface of a uniform reflectance. The section 16 stores, in units of one pixel, data concerning image nonuniformity due to nonuniformity in the illumination of the illumination section 1 or variations in the properties of the image pickup elements of the line sensor camera 4.

The feature storage 21 stores part of an image, and can read and write an image of a particular range. The feature storage 21 stores images of a plurality of those characterizing portions of the to-be-inspected object 5, which determine the coordinates of the object 5, and also stores the coordinates of the images. The image storage 240 stores an image of an ideal to-be-inspected object 5.

Information on defects extracted by the defect extraction algorithms 40 and 41 is supplied to a defect judging section 32 as good or bad judging means, where it is determined whether or not the to-be-inspected object 5 has a defect, i.e. whether or not the to-be-inspected object 5 is good, and the type of the defect is determined, using data accumulated in a defect dictionary 31. If it is determined that the to-be-inspected object 5 is defective, the image data indicating this fact is automatically stored in the database 45. Further, a display 29 displays a result of determination as to whether or not the to-be-inspected object 5 should be guided to the downstream side of the production line. The display 29 displays an image corrected by the aforementioned image position correcting section 20, also displays the position of a defect by, for example, coloring it on the image in accordance with the type of the defect, and displays the coordinates of the position and the determination result, etc.

The communication data storage 46 of the host computer 49 is connected to an operation/input section 43. The operation/input section 43 is also located outside the clean room 53, and outputs various types of instructions from the communication data storage 46 to each client computer 48 via the LAN 47.

As shown in FIG. 1, each client computer 48 is located inside the clean room 53, as well as a corresponding inspection apparatus 60 equipped with the defect image pickup section 50 and various control sections.

The above structure can be modified such that pairs of inspection apparatuses 60 and client computers 48 are arranged in respective clean rooms 53 located along manufacturing lines in factories situated in different separate areas (domestic or overseas areas), and each client computer 48 is connected, via a communication line, to the host computer 49 and the database 45 installed in a control center. In this case, a telephone line or the Internet that connects domestic areas and overseas areas by a communication network can be used as the communication line.

Figure 2:
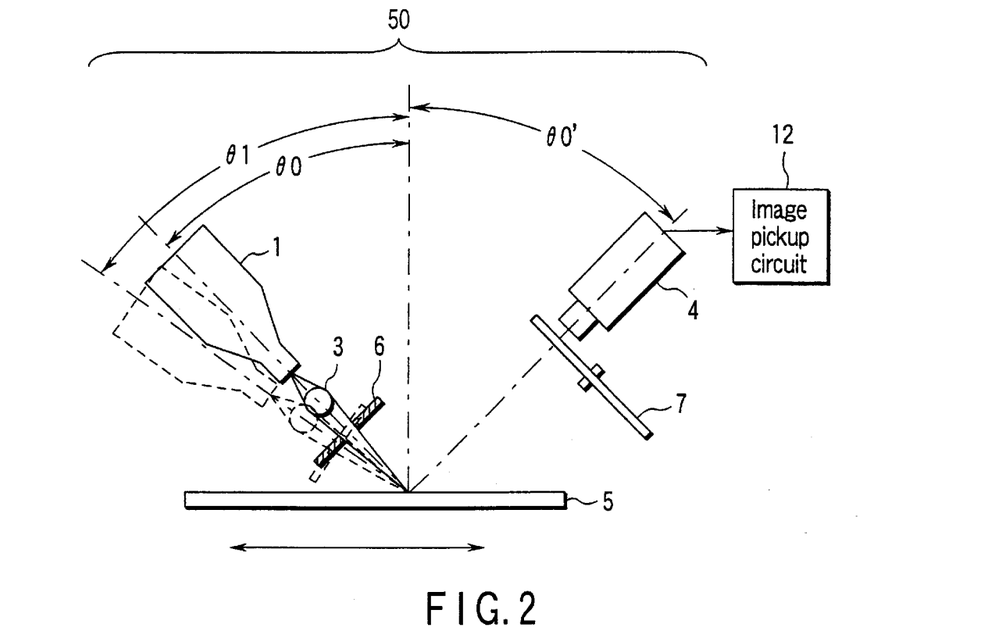
FIG. 2 is a schematic view illustrating a structure of a defect image pickup section according to the embodiment of the invention.

FIG. 2 is a schematic view illustrating a structure of the defect image pickup section 50. The defect image pickup section 50 constitutes a digital macro inspection apparatus.

In FIG. 2, the illumination section 1 has a light source and an optical system for line illumination. A lamp housing equipped with a halogen lamp, a heat-wave absorbing filter and a condenser lens is used as the light source for illumination. Further, the optical system for illumination is formed of a condenser lens for converging a light flux from the lamp housing, and a fiber bundle.

The illumination section 1 is movable with respect to the to-be-inspected object 5, and is disposed to emit light in line to the surface of the object 5 at incident angle θ0. A cylindrical lens 3 for converging a light flux, and a slit 6 are interposed between the illumination section 1 and the to-be-inspected object 5. The illumination section 1, the cylindrical lens 3 and the slit 6 are integrated into one structure, which can have its angle varied voluntarily relative to the surface of the to-be-inspected object 5, and can illuminate the surface of the to-be-inspected object 5 at incident angle θ1.

The line sensor camera 4 is provided in a position opposed to the illumination section 1 via the filter 7. The line sensor camera 4 picks up an image of a linear area of the illuminated object 5. The filter 7 is a narrow band filter for limiting the wavelength band of the illumination light to obtain an interference image. The filter 7 is located in front of the line sensor camera 4 and can be arranged to cross and be moved away from the optical path. The defect image pickup section 50 is located in a dark box (not shown) so as not to be influenced by outside light.

Figure 3:
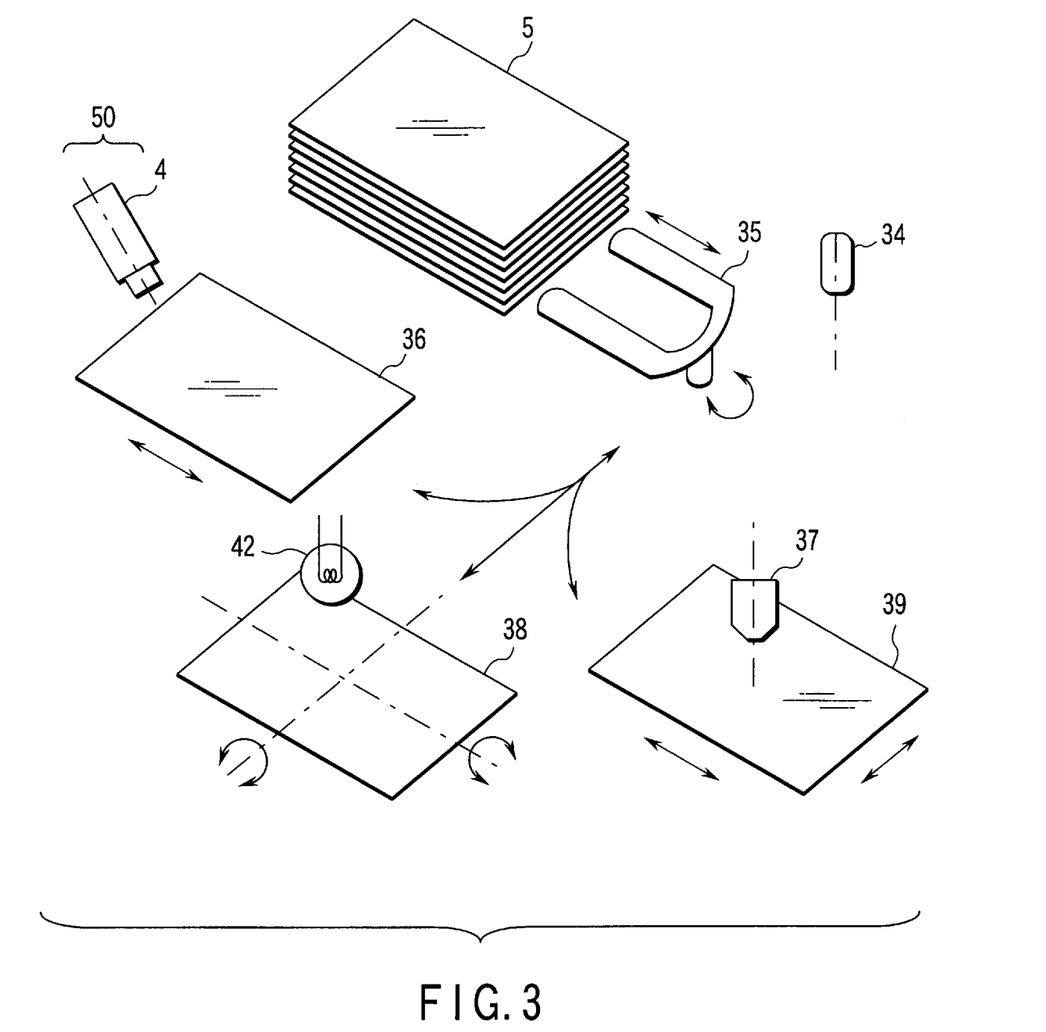
FIG. 3 is a view illustrating a process of conveying a to-be-inspected object according to the embodiment of the invention.

FIG. 3 is a view illustrating an inspection process executed by an FPD substrate outward appearance inspection system equipped with the digital macro inspection function of the defect inspection data processing system, a digital micro inspection function and a macro inspection function. The host computer 49 controls each inspection station provided for the inspection process via each client computer 48.

In the inspection process, at first, a plurality of to-be-inspected objects 5 supplied from the upstream side of the production line are carried by a sample conveyance carrier (its frame is not shown) and thus placed in the system. The drive section 22 drives a robot 35 in accordance with an instruction from the drive control section 13 shown in FIG. 1, so that the robot takes a predetermined to-be-inspected object 5 out of the carrier and conveys it to, for example, the stage of each inspection station, or returns an already inspected object 5 to the carrier.

The defect image pickup section 50 (this section is the same as that shown in FIG. 2, but only the line sensor camera 4 incorporated in it is shown in FIG. 3) is located above a one-axle stage 36 that constitutes a digital macro inspection station. When the conveyance robot 35 has conveyed a to-be-inspected object 5 onto the one-axle stage 36, the stage drive section 15 moves the to-be-inspected object 5 along the one axle, together with the one-axle stage 36, in response to an instruction from the drive control section 13. While the to-be-inspected object 5 is being moved, the line sensor camera 4 picks up an image of the entire surface of the object 5, and after that, defect detection is executed.

A swingable stage 38 has a two-axle rotary mechanism that constitutes a visual-check macro inspection station. The operator can change the angle of the swingable stage 38 while observing the to-be-inspected object 5. Further, while illuminating the to-be-inspected object with an illumination device 42 provided above it, the operator can visually detect a flaw, dust or defect on the to-be-inspected object 5. A macro-observation control section 30 controls the swingable stage 38 in accordance with an instruction from the drive control section 13.

A microscope 37 (only the objective of which is shown in FIG. 3) for realizing micro observation is located above a two-axle stage 39 that constitutes a micro inspection station. The two-axle stage 39 enables the to-be-inspected object 5 to be moved two-dimensionally and enables a to-be inspected portion of the object to be aligned with the optical axis of the microscope 37. As a result, any voluntarily-selected portion of the to-be-inspected portion of the object 5 can be magnified and inspected. The microscope stage drive section 26 controls the two-axle stage 39 in accordance with an instruction from the drive control section 13.

A position sensor 34 is provided above a path through which the robot 35 is conveyed. The position sensor 34 detects the position and orientation of the to-be-inspected object 5 while the robot 35 is conveying the to-be-inspected object 5. Information from the position sensor 34 is supplied to the drive control section 13 via the sample-orientation adjusting/detecting section 25. On the basis of the information, the drive control section 13 controls the robot 35 via the sample conveyance control section 22. As a result, the amount of movement of the to-be-inspected object 5 to, for example, each stage, onto which the object 5 is mounted, is adjusted, and the position of the object is aligned. Thus, the to-be-inspected object 5 is always adjusted in the same relative position on the stage of each station.

As described above, the robot 35 conveys the to-be-inspected object 5 onto the one-axle stage 36, the swingable stage 38 and the two-axle stage 39, so that the object 5 assumes the same relative position on each of the stages, thereby enabling stable observation.

The operation of the system constructed as above will now be described. First, a carrier with a plurality of to-be-inspected objects 5 received therein is moved from the upstream side of the production line into the FPD substrate outward appearance inspection system installed in the clean room 53, manually or by a conveyance device employed in the production line.

Subsequently, a signal indicative of the start of an inspection is input to the operation/input section 43 shown in FIG. 1, manually or by the conveyance device of the production line, thereby starting the operation of the system. When the start signal is input to the operation/input section 43, each client computer 48 executes the following operation.

When an instruction to move a to-be-inspected object 5 has been output from the drive control section 13 to the sample conveyance control section 22, the robot 35 shown in FIG. 3 takes a predetermined to-be-inspected object 5 out of the carrier and moves it to the underside of the position sensor 34. The position sensor 34 detects the position or orientation of the to-be-inspected object 5, and supplies information indicative of the detection result to the drive control section 13 via the sample-orientation adjusting/ detecting section 25 shown in FIG. 1.

On the basis of the information indicative of the present position of the to-be-inspected object 5, the drive control section 13 calculates a distance to the one-axle stage 36, through which the object is to be moved next, and supplies the sample conveyance control section 22 shown in FIG. 1 with an instruction to move the object. As a result, the robot 35 can always place the to-be-inspected object 5 in the same position and direction on the one-axle stage 36.

After the to-be-inspected object 5 is accurately placed on the one-axle stage 36, the drive control section 13 outputs an instruction to the stage drive section 15, thereby moving the to-be-inspected object 5 together with the one-axle stage 36 along the one axle. While the to-be-inspected object 5 is moving along the one axle, light emitted from the illumination section 1 of FIG. 2 and converged by the cylindrical lens 3 and the slit 6 is applied to the surface of the to-be-inspected object 5 at incident angle $\theta 0$.

The flux of light reflected from a linear portion of the illuminated to-be-inspected object 5 enters the filter 7 that crosses the optical path, whereby only light of a predetermined wavelength forms an image on the line sensor camera 4. At this time, if the film formed on the surface of the to-be-inspected object 5 is uneven, interference occurs in light having passed through the filter 7, and hence the unevenness of the film is detected in terms of changes in the amount of light.

The line sensor camera 4 converts image forming light into an electric signal, and transmits the signal to the image pickup circuit 12 in units of one line. The image pickup circuit 12 converts an electric signal corresponding to each line into image data while the to-be-inspected object 5 is moving, thereby constructing two-dimensional image data. After the image pickup circuit 12 creates image data corresponding to the entire object 5, the image data is stored in the database 45 via the communication data storage 44 and the LAN 47.

Subsequently, the drive control section 13 of FIG. 1 outputs an instruction to the filter drive section 10, thereby moving the filter 7 of FIG. 2 away from the optical path. At the same time, the section 13 outputs an instruction to the illumination angle adjusting section 18, thereby changing, to incident angle $\theta 1$, the angle of illumination of the illumination section 1 relative to the to-be-inspected object 5.

After that, the drive control section 13 outputs an instruction to the stage drive section 15, thereby moving the to-be-inspected object 5 along the one axle in a direction opposite to the above in FIG. 2. Although, at this time, the to-be-inspected object 5 is illuminated in a similar manner to the above, that part of a light flux emitted from the illumination section 1, which has incident angle $\theta 0$, is interrupted by the slit 6, and only a light flux of incident angle $\theta 1$ strikes the to-be-inspected object 5.

Since the line sensor camera 4 is also located at angle $\theta 0$ to the to-be-inspected object 5, a light flux regularly reflected from the to-be-inspected object 5 does not enter the line sensor camera 4, if the to-be-inspected object 5 does not have any unevenness. If, however, the to-be-inspected object 5 has a flaw, dust, defect or pattern, part of a light flux entering the object at incident angle $\theta 1$ reflects therefrom at reflection angle $\theta 0'$ (=$\theta 0$) and enters the line sensor camera 4.

After the image pickup circuit 12 constructs two-dimensional image data indicative of the entire object 5 on the basis of the light entering the line sensor camera 4, the constructed image data is transmitted to the database 45 via the communication data storage 44 and the LAN 47, and stored therein.

Similarly, image data on the to-be-inspected object 5 fetched by each client computer 48 is stored in the database 45. At the same time, the host computer 49 reads a plurality of image data items from the database 45 and stores them in the image storage 8 via the communication data storage 46. Thereafter, the defect extraction algorithms 40 and 41 execute image processing on each image data item stored in the image storage 8.

In this case, the image nonuniformity storage 16 pre-stores information concerning image nonuniformity due to nonuniformity in the illumination of the illumination section 1 or variations in the characteristics of the image pickup elements of the line sensor camera 4. The feature storage 21 pre-stores the features of the to-be-inspected object 5. Further, the image storage 240 pre-stores an image of an ideal to-be-inspected object 5. The setting of the image nonuniformity or features is executed in the following manner.

First, the line sensor camera 4 picks up, instead of the to-be-inspected object 5 and under the illumination system of incident angle θ0, a sample substrate having an ideal mirror surface (such as a master substrate with a nondefective mirror surface) or having a uniform reflectance over the entire surface thereof. The image storage 8 stores its image data. Since, in this case, an image of an object having a uniform reflectance over the entire surface thereof is picked, the resultant two-dimensional image data must indicate its uniform surface. Actually, however, vertical stripes occur in the image because of nonuniformity in the illumination or variations in the characteristics of the image pickup system. In light of this, one-dimensional data, which is obtained by setting, at "0", the brightness of a pixel of the lowest brightness included in the pixels that correspond to the vertical stripes, is stored as image nonuniformity information in the image nonuniformity storage 16. This processing is executed using an image processing algorithm (not shown).

It is difficult to obtain a master substrate with an ideal mirror surface or a sample substrate having a uniform reflectance over the entire surface thereof. It is also difficult to maintain their initial conditions. Therefore, actually, it is sufficient if the average of the brightnesses of pixels in each vertical line of a two-dimensional image picked by the line sensor camera 4 is calculated, one-dimensional data is created by setting the lowest average value at "0", and is stored as image nonuniformity information in the image nonuniformity storage 16. In this case, the influence of microscopic dirt or dust, if there is any, can be ignored.

The image storage 8 stores an image of the to-be-inspected object 5 picked by the optical system at incident angle θ0, and an image of the object 5 picked, at incident angle θ1, by the optical system from which the narrow-band filter 7 is removed. From these two images, the operator designates a characterizing portion of the to-be-inspected object 5, which is suitable for specifying the orientation or position of the object 5, and stores the characterizing portion in the feature storage 21. In this case, the characterizing portion indicates, for example, an image of each corner of a rectangular to-be-inspected object 5, a recognition mark attached to the to-be-inspected object 5, or a notch or orientation flat of a semiconductor wafer. The positioning accuracy of image coordinates can be further enhanced by storing data on a plurality of characterizing portions of each image picked at incident angle θ0 or θ1.

The image storage 240 stores a plurality of images of ideal to-be-inspected objects 5.

A description will now be given of the operation of each defect extraction algorithm, which is executed when data is preset in the image nonuniformity information storage 16, the feature storage 21 and the image storage 240.

Image data items picked at incident angles θ0 and θ1 and stored in the image storage 8 are processed in a parallel manner by the defect extraction algorithms 40 and 41, respectively. The image data supplied to the defect extraction algorithm 41 is subjected to a nonuniformity removal process executed in the image nonuniformity removing section 11, in which data stored in the image nonuniformity storage 16 is added over the entire image thereby to remove nonuniformity in illumination or in the optical system.

Subsequently, the characterizing-portion extracting section 17 compares the image of a portion designated by the operator with an image stored in the feature storage 21, thereby detecting whether or not the coordinates of the to-be-inspected object 5 in the image are deviated vertically or in the direction of rotation. If they are deviated, the image position correcting section 20 corrects the deviations. The corrected data is displayed on the display 29, and the operator can inspect an image of the to-be-inspected object 5.

The image having its deviations corrected by the image position correcting section 20 is supplied to the defect extraction section 24. The defect extraction section 24 compares the image with an image of an ideal to-be-inspected object 5 stored in the image storage 240, thereby removing a to-be-inspected-object outline image as an image inherent to a to-be-inspected object, an outline image within an exposure range or a predetermined pattern image, etc., so as to extract only a defective portion.

The defect coordinate extracting section 28 extracts the coordinates of the defective portion in the image extracted by the defect extraction section 24, and supplies the coordinate data to the drive control section 13. In addition to this, the defect coordinate extracting section 28 extracts the tint, size or coordinates of the defective portion extracted by the defect extraction section 24, and supplies the extracted data to the defect judging section 32.

Similarly, the defect extraction algorithm 40 executes defect extraction on image data different from that processed by the defect extraction algorithm 41, and supplies the extraction result to the drive control section 13 and the defect judging section 32. The defect judging section 32 reads information on defects pre-stored in the defect dictionary 31.

The defect judging section 32 compares data, such as the tint, size or coordinates of each defect supplied from the two defect extraction algorithms 40 and 41, with the defect information read from the defect dictionary 31. Furthermore, the defect judging section 32 judges the type of each defect, names it, judges whether or not the to-be-inspected object 5 should be guided to the downstream side of the production line, thereby displaying the judgment result on the display 29.

The ratio of the number of areas including defects to the number or the total area of defects extracted by the defect extraction algorithms 40, 41 (or to the total number of small areas (dies) of the same shape exposed on the to-be-inspected object) may be used as a judgment standard. Furthermore, the determination as to whether or not the object is good may be performed by determining the type of defect as a result of comparison using the defect dictionary 31, and providing, for each type of defect, a judgment standard concerning the number or total area of defects, or the number of areas including defects.

The display 29 displays an image corrected by the image position correcting section 20, and also displays the position of each defect indicated in a color, the coordinates of the position and a judgment result, etc.

After the defect detection process is finished, the drive control section 13 shown in FIG. 1 outputs an instruction to the sample conveyance control section 22 so as to make the robot 35 shown in FIG. 3 remove the to-be-inspected object 5 from the one-axle stage 36 and convey the object 5 to the swingable stage 38 that constitutes the visual-check macro inspection station.

When the to-be-inspected object 5 has been placed on the swingable stage 38 shown in FIG. 3, the macro illumination device 42 illuminates the entire surface of the to-be-inspected object 5. As a result, the operator can visually inspect the entire surface of the to-be-inspected object 5. At this time, the drive control section 13 waits an input from the operation/input section 43. If, in this state, the operator has operated at hand, for example, a joy stick incorporated in the operation/input section 4, the drive control section 13 outputs an instruction to the macro-observation control section 30, thereby driving the swingable stage 38 in directions indicated by the arrows in FIG. 3 so as to swing the to-be-inspected object 5 to and fro and from side to side. Thus, the to-be-inspected object 5 can be moved angularly so that the operator can easily inspect it. In other words, the operator can set the angle of the to-be-inspected object 5 so that they can visually detect a defect.

If the operator would like to newly register the type or name of a defect detected by visual check, they input data by operating, for example, the keyboard of the operation/input section 4 located at hand. This data is stored in the database 45 via the communication data storage 44 and the LAN 47. Further, this data can be input to the host computer 49 and registered in the defect dictionary 31 shown in FIG. 1.

If the operator would like to stop the visual check, or if a preset period in time has elapsed, the drive control section 13 outputs an instruction to the sample conveyance control section 22 so as to make the robot 35 remove the to-be-inspected object 5 from the swingable stage 38 and convey the object 5 to the two-axle stage 39 that constitutes the digital micro inspection station.

When the to-be-inspected object has been placed on the two-axle stage 39 shown in FIG. 3, the drive control section 13 outputs an instruction to the microscope stage drive section 26 under the control of the host computer 49, thereby moving the two-axle stage 39 together with the to-be-inspected object 5 so that the optical axis of the microscope 37 is positioned at the coordinates of a defect extracted by the defect coordinate extracting section 28 of FIG. 1. The microscope 37 enlarges a portion of the to-be-inspected object 5, and a CCD camera 52 attached to the microscope 37 picks up an image of the enlarged portion. This image is supplied to the host computer 49 via the communication data storage 44 and the LAN 47, and displayed on the display 29. Thus, the operator can see a minute defective portion of the to-be-inspected object 5. At this time, the drive control section 13 waits an input from the operation/input section 43.

If, in this state, the operator has operated the operation/input section 43, the drive control section 13 outputs an instruction to the microscope stage drive section 26 under the control of the host computer 49, thereby moving the to-be-inspected object 5 to and fro and from side to side as shown in FIG. 3 to situate it in any voluntarily selected position. As a result, the operator can situate a defect in the center of the field of vision of the display 29, and can see the defect in more detail on the display 29. If the operator would like to newly register the type or name of the defect detected by microscopic observation, they can register it in the defect dictionary 31 by operating the operation/input section 43 as in the case of the visual check.

If the operator would like to finish the microscopic observation, or if a preset period in time has elapsed, the drive control section 13 outputs an instruction to the sample conveyance control section 22 so as to make the robot 35 remove the to-be-inspected object from the two-axle stage 39 and store the object 5 in the carrier.

Further, if to-be-inspected objects 5 are left in the carrier, the drive control section 13 causes them to be sequentially conveyed and subjected to the above-described series of inspection processes. After all to-be-inspected objects 5 contained in the carrier are inspected, the series of operations are finished, and the system is in the standby state until the next carrier is mounted thereon.

Although in the above embodiment, a single host computer 49 is employed, a plurality of host computers may be used. In this case, the required internal process functions may be distributed in the host computers.

Further, the roles of the host computer 49, each client computer 48 and the database are not limited to the above-described ones. For example, the host computer 49 may have a function corresponding to that of the database 45. Furthermore, a microscopic image of a portion, which is determined defective (NG), may automatically be stored in the database 45, so that the operator can inspect it on the display 29 later.

Also, the operation/input section 43 may be connected to the communication data storage 49 of each client computer 48, instead of the structure in which the operation/input section 43 is connected only to the communication data storage 46 of the host computer 49. Alternatively, the operation/input section 43 may be connected to the LAN 47 or to another communication line. Moreover, the image nonuniformity storage 16, the feature storage 21 and the image storage 240 may be installed not in the host computer 49 but in the database 45.

If the operation/input section 43 is connected to a communication line, each client computer 48 can be operated from a faraway place. In particular, in a clean room of a very high degree of cleanliness, to minimize the influence of dust raised when an inspector enters the clean room, it is desirable that they should not enter the clean room unless they need to enter the room to execute, for example, a visual inspection. The remote control of each client computer using a communication line enables most inspections and operations to be executed outside the clean room. As a result, the occasions of the entrance of inspectors into the clean room can significantly be reduced, thereby maintaining a high degree of cleanliness.

The display 29 and the operation/input section 43 may be integrated as one body such as a touch panel. Further, the above embodiment describes an example of an inspection procedure for each to-be-inspected object 5. This procedure of inspection, however, may be changed, or some of the inspection processes may be omitted.

The defect detection function (defect detection algorithm) employed in the host computer 49 may be installed in both the host computer 49 and each client computer 48, or installed only in each client computer 48. In this case, the image pickup circuit 12 of each client computer 48 is connected to the image storage 8, which is connected to the characterizing-portion extracting section 17. The characterizing-portion extracting section 17 is further connected to the defect extraction section 24 and the feature storage 21. The provision of a defect detecting function at the client computer 48 side enables defect detection to be executed when an image of a to-be-inspected object 5 is fetched by each client computer 48. This means that the defect detection process can be performed at high speed, and the processing load on the host computer 49 side can be reduced.

In addition, the host computer 49 can appropriately update a recipe related to defect detection, record the recipe in the database 45 via the LAN 47 of another communication line, and distribute it to each client computer 48 via the database 45.

Since, in the embodiment, each client computer 48 having the defect image pickup section 50 is separate from the host computer 49 having the defect detecting function and a good/bad determining function, the each client computer 48 can be installed in the clean room 53, and the host computer 49 and the operation/input section 43, etc. can be arranged outside the clean room 53. Therefore, even when installing a plurality of client computers 48 to enhance the efficiency of inspection, the size of the clean room 53 can be minimized, thereby reducing the cost required for the equipment. Thus, the system of the embodiment is economically advantageous.

Further, since only the main body of each inspection apparatus 60 and each client computer 48 are located in the clean room 53, the number of occasions of the entrance of inspectors into the clean room 53 is significantly reduced, thereby remarkably enhancing a dust-proof effect.

Moreover, since an operation instruction from the operation/input section 43 is transmitted to each client computer 48 side via a communication line such as the LAN 47, each inspection apparatus 60 can be controlled from a faraway place. If each visual-check macro inspection station is automated using a CCD camera to enable observation with a monitor, it can be controlled from a faraway place, using the operation/input section 43.

An image of the to-be-inspected object 5 picked by the defect image pickup section 50 and obtained via each client computer 48 is temporarily stored in the database 45 and then subjected to defect detection while it is being fetched by the host computer 49. Accordingly, image data can be commonly used, and the host computer 49 can efficiently execute the process of detecting a defect.

As compared with the time required for picking up an image of the to-be-inspected object 5 under the control of each client computer 48, the time required for data analysis for defect determination executed in the host computer 49 is sufficiently short. This means that defect detection on the to-be-inspected object 5 is executed almost within the time required for data analysis.

Until the host computer 49 detects a defect, the operator does not have to perform any operation related to the detection and hence can perform another job in a parallel manner.

The host computer 49 concentrically processes image data transmitted from each client computer 48, which enables a skilled inspector to judge whether or not each image data item is good. This being so, the judgment level concerning the image data from each client computer 48 can be maintained constant thereby to enhance the accuracy of the entire defect inspection process. Furthermore, the concentric management of a large amount of image data supplied from a number of client computers 48 enables early collection of new defective image data as a material to be determined good or bad, thereby enhancing the reliability of the defect dictionary 31 or that of a recipe related to defect detection.

The present invention is not limited to the above-described embodiment, but can be modified appropriately without changing the gist.

The present invention provides a compact and economical defect inspection data processing system that enables a plurality of defect detection apparatuses to execute defect inspection efficiently and accurately.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A defect inspection data processing system comprising:
   an inspection device provided in a clean room and having an image pickup section for picking up a two-dimensional image of a to-be-inspected object to be processed in a manufacturing process in the clean room;
   a client computer connected to the inspection device and having a data transfer section for transferring data indicative of the image picked by the image pickup section;
   a communication line;
   a database for storing image data transferred from the client computer via the communication line; and
   a host computer provided outside the clean room and connected to the communication line and including a defect extraction section for extracting defect information from the image data stored in the database, and a good/bad judgment section for judging whether or not the to-be-inspected object is good in accordance with judgment criteria including at least one of a number of defects, an area of defects and a number of defect regions, based on the defect information extracted by the defect extraction section.

2. The defect inspection data processing system according to claim 1, wherein a plurality of inspection devices are provided for the manufacturing process in the clean room and a plurality of client computers are respectively connected to the plurality of inspection devices, and one host computer disposed outside the clean room is connected via the communication line to each of the client computers connected to the inspection devices.

3. The defect inspection data processing system according to claim 2, wherein the inspection devices and the client computers are respectively arranged in the clean room in each of a plurality of factories located in different areas, and the client computers are connected via the communication line to the host computer set in a control center.

4. The defect inspection data processing system according to claim 1, wherein the database is provided outside the clean room via the communication line.

5. The defect inspection data processing system according to claim 1, wherein the good/bad judgment section compares the defect information extracted by the defect extraction section with defect data registered in a predetermined defect dictionary to thereby determine a type of defect and whether the defect is good or bad, stores image data of a defect judged to be bad in the database, and displays a judgment result on a display.

6. The defect inspection data processing system according to claim 1, wherein the host computer updates a recipe for a new defect to be judged to be good or bad by the good/bad judgment section by a type of defect and a name of defect registered by an operation/input section, stores the recipe in the database via the communication line, and distributes the recipe from the database to the client computer.

7. The defect inspection data processing system according to claim 1, wherein the host computer connects an image storage section for storing image data picked by the image pickup section to the communication line via a communication data storage section, thereby connecting the defect detection section to the image storage section in a parallel manner.

8. The defect inspection data processing system according to claim 1, wherein the defect extraction section includes an image non-uniformity storage section that pre-stores image non-uniformity data resulting due to non-uniform illumination and non-uniformity in characteristics of image pickup elements, for each of a plurality of pixels, based on image data obtained by picking up a non-defective substrate or a sample having a uniform reflectance over an entire mirror surface thereof, and an image non-uniformity removing section for removing a non-uniformity from the image data using the image non-uniformity data stored in the image non-uniformity storage section.

9. The defect inspection data processing system according to claim 8, wherein the image pickup element comprises a line sensor camera disposed to be normal to a direction of a relative movement with respect to the to-be-inspected object, and wherein one-dimensional data obtained by setting to "0" a lowest brightness of a pixel obtained by picking up an image of a non-defective substrate with the line sensor camera is stored as the image non-uniformity data in the image non-uniformity storage section.

10. The defect inspection data processing system according to claim 8, wherein the image pickup element comprises a line sensor camera disposed to be normal to a direction of a relative movement with respect to the to-be-inspected object, and wherein the image non-uniformity storage section obtains an average brightness of pixels of lines of a two-dimensional image picked up with the line sensor camera by moving the camera in one direction relative to the non-defective substrate, and stores one-dimensional data obtained by setting a lowest value to "0" as the image non-uniformity data in the image non-uniformity storage section.

11. The defect inspection data processing system according to claim 1, wherein the defect extraction section further includes a feature storage section for storing an image and coordinates of a characterizing portion of the to-be-inspected object, which determines coordinates of the to-be-inspected object, a characterizing-portion-extracting section for comparing the image stored in the feature storage section with image data read from the database to obtain a displacement therebetween, and an image position correcting section for correcting the displacement obtained by the characterizing-portion-extracting section.

12. The defect inspection data processing system according to claim 1, wherein:

the inspection device comprises a digital macro inspection section having a macro image pickup unit for obtaining an entirety of the to-be-inspected object to be processed in the manufacturing process as a two-dimensional image, and a digital micro inspection section having a micro image pickup unit for obtaining a two-dimensional image of a defective portion detected by the digital macro inspection section, by magnifying a view of a portion under a microscope; and the host computer sends position information of a defect extracted by the defect detection section from the macro image data sent from the digital macro inspection section, via the communication line, to the client computer of the digital micro inspection section, and automatically aligns the defect with an observation optical axis of the microscope by controlling a biaxial stage of the digital micro inspection section, and remotely manipulates the biaxial stage of the digital micro inspection section in accordance with manipulation by an operator of an operation/input section connected to the host computer.

13. The defect inspection data processing system according to claim 12, wherein the host computer automatically stores a micro image of a defective portion judged to be bad by the good/bad judgment section, that is magnified under the microscope, in the database.

14. The defect inspection data processing system according to claim 12, wherein:

the digital macro inspection section further comprises a line sensor camera and a line illumination section that are arranged to be normal to a direction of a relative movement of a uniaxial stage on which the to-be-inspected object is placed, and a swingable stage on which the to-be-inspected object is placed, and a macro illumination section and a CCD camera provided above the swingable stage, and the host computer displays a macro image of the to-be inspected object picked up with the CCD camera on a display located on a host computer side and remotely manipulates the swingable stage in accordance with manipulation of the operation/input section by the operator.

* * * * *